US005919488A

United States Patent [19]

Yamaji

[11] Patent Number: 5,919,488

[45] Date of Patent: Jul. 6, 1999

[54] ANTIMICROBIAL AQUEOUS DISPERSION

[75] Inventor: Munetoshi Yamaji, Koshigaya, Japan

[73] Assignee: SOMAR Corporation, Japan

[21] Appl. No.: 09/017,621

[22] Filed: Feb. 2, 1998

[30] Foreign Application Priority Data

Feb. 20, 1997 [JP] Japan .................................... 9-036355

[51] Int. Cl.[6] ............................ A61K 9/16; A61K 31/50; A61K 31/425; A61K 31/415

[52] U.S. Cl. .......................... 424/494; 514/247; 514/365; 514/402; 514/494; 514/937

[58] Field of Search .................................... 514/247, 365, 514/402, 494, 937; 424/494

[56] References Cited

U.S. PATENT DOCUMENTS 5,643,971 7/1997 Roenigk .................................. 523/122

FOREIGN PATENT DOCUMENTS 8-34802 2/1996 Japan .
9-40703 2/1997 Japan .

*Primary Examiner*—Kevin E. Weddington
*Attorney, Agent, or Firm*—Wenderoth, Lind & Ponack, LLP

[57] ABSTRACT

Disclosed is a novel aqueous suspension of an antimicrobial compound having high stability of the suspension despite the use of such a very small amount of a suspending agent as not to cause any adverse influences on the inherent activity of the active ingredient. The suspending agent is a biocellulose as a microbial products of certain acetic bacteria which is not used in the prior art as a suspending agent in the prior art due to susceptibility to putrefaction while this defect of the biocellulose can be solved in the antimicrobial aqueous suspension by the use of an antimicrobial compound such as 2-methoxycarbonylamino benzimidazole, 2-pyridinethiol zinc-1-oxide and 2-(4-thiazolyl) benzimidazole.

5 Claims, No Drawings

ANTIMICROBIAL AQUEOUS DISPERSION

BACKGROUND OF THE INVENTION

The present invention relates to a novel antimicrobial aqueous dispersion or, more particularly, to an aqueous dispersion of fine particles of an antimicrobially effective compound hardly soluble in water as suspended in an aqueous medium containing a unique suspending agent.

It is a well established technology that various kinds of water-insoluble or hardly water-soluble solid compounds are employed in practical applications in the form of an aqueous suspension prepared by uniformly dispersing fine particles of the compound in an aqueous medium containing a so-called suspending agent having activity to stabilize the aqueous dispersion of the solid particles of the compound by preventing settling of the particles. The suspending agent currently under use is a water-soluble polymeric or water-dispersible compound exemplified by natural and synthetic polymers including gelatine, gum arabic, tragacanth, sodium alginate, bentonite, methylcelluose, salts of carboxymethyl cellulose, polyvinyl alcohol, salts of polyacrylic acid and the like. These suspending agents are used as selected depending on the particular solid material to be dispersed in the aqueous medium. In many cases, suspending agents are used in combination with a surface active agent as an emulsifying agent.

A problem in the use of these conventional suspending agents is that the suspending effect by the use of a suspending agent can be fully exhibited only by the use of a relatively large amount thereof requiring an amount of, for example, 2% by weight or even larger based on the total amount of the aqueous suspension. Therefore, a disadvantage is sometimes unavoidable in an aqueous suspension of a food or a medicament compound that the tastiness of the food or medicinal effectiveness of the medicament per se is adversely affected by the suspending agent so that the amount of the suspending agent must be decreased at the sacrifice of the suspending effect.

On the other hand, it is known that a biocellulose is produced when various kinds of acetic bacteria such as *Acetobacter aceti, Acetobacter pasteurianus, Acetobacter aceti* var. *xylinam* and the like are grown. The biocellulose obtained by this microbial method has a high purity as compared with conventional plant-origin celluloses and the degree of crystallinity, degree of polymerization and water-absorptivity can be easily controlled by selecting the culturing conditions of the bacteria so that biocelluloses are highlighted in recent years as a novel base material in various industrial fields.

Biocelluloses, however, are in general not free from problems and disadvantages. Since biocelluloses serve as a nutrient for the growth of certain bacteria and fungi, for example, they are susceptible to putrefaction or denaturation not to be storable for a long term at room temperature requiring refrigerating conditions for long-term storage in a refrigerator.

The above mentioned disadvantage of a biocellulose limits the industrial application fields of biocelluloses as a substitute for plant-origin celluloses and the only applications heretofore developed include the use thereof as an extender of paper products and as a filler in the paper sheets for loudspeaker cones and data cards.

SUMMARY OF THE INVENTION

The present invention has an object, in view of the above mentioned situations in the aqueous suspension of various kinds of active ingredients relative to the performance of the suspending agent, to provide a novel antimicrobial aqueous suspension prepared by using a unique suspending agent which has no adverse influences on the performance of the antimicrobially effective ingredient as the dispersant of the aqueous suspension.

Thus, the antimicrobial aqueous suspension provided by the present invention is a uniform dispersion which comprises:

(A) an aqueous medium containing a biocellulose as the dispersion medium of the suspension; and (B) particles of an antimicrobially active, hardly water-soluble compound dispersed in the aqueous medium, the amount of the biocellulose being in the range from 0.1 to 5.0% by weight based on the overall amount of the aqueous suspension.

DETAILED DESCRIPTION OF THE PREFERRED EMBODIMENTS

As is described above, the most characteristic feature of the inventive antimicrobial aqueous suspension consists in the use of a biocellulose as a suspending agent of the antimicrobially active compound in an aqueous dispersion medium.

This feature of the invention is based on the discovery accomplished as a result of the extensive investigations undertaken by the inventor with an object to develop an aqueous antimicrobial suspension free from the above described disadvantages in the prior art suspensions arriving at an idea that a biocellulose might serve as an effective suspending agent for a hardly water-soluble antimicrobial compound. In this case, the above mentioned most serious defect of biocelluloses of susceptibility to microbial putrefaction is of course of no matter in the presence of particles of an antimicrobially active compound.

The present invention is applicable to any antimicrobially effective compounds provided that the compound is hardly soluble in water or, namely, has a very limited solubility of, for example, several hundreds of ppm by weight or less in water. Examples of antimicrobial compounds to which the present invention is applicable include 2-methoxycarbonylamino benzimidazole, 2-pyridinethiol zinc-1-oxide, 2-(4-thiazolyl) benzimidazole and the like either singly or as a combination of two kinds or more according to need. A combination of 2-methoxycarbonylamino benzimidazole and 2-pyridinethiol zinc-1-oxide in a weight proportion of 100:1 to 1:100 or, preferably, 50:1 to 1:50 exhibits particularly high microbicidal and growth-preventing activity to various kinds of bacteria and fungi.

Particles of the above mentioned antimicrobial compound or compounds are dispersed in an aqueous medium containing a biocellulose as the suspending agent to form a stable aqueous suspension. The amount of the biocellulose contained as the suspending agent in the aqueous medium is in the range from 0.1 to 5.0 parts by weight or, preferably, from 0.2 to 2.0 parts by weight per 100 parts by weight of the overall amount of the aqueous suspension. When the amount of the suspending agent is too small, the suspending effect thereof cannot be fully exhibited so that a decrease is caused in the stability of the aqueous suspension while, when the amount of the suspending agent is too large, the problem of putrefaction cannot be completely disregarded even in the presence of the antimicrobial compound, though dependent on the antimicrobial activity thereof.

The amount of the suspending agent should also be specified relative to the amount of the particles of the antimicrobial compound to be suspended in the aqueous medium. Namely, the weight proportion of the biocellulose to the solid particles to be suspended is in the range from 1:300 to 10:1 or, preferably, from 1:100 to 1:1 or, more preferably, from 1:100 to 1:10.

The suspending effect exhibited by the biocellulose is so strong that particles of the antimicrobial compound can be suspended in the aqueous medium with full stability even without using a surface active agent in combination although use of a surface active agent in combination with the biocellulose has no particular adverse influences.

The antimicrobial aqueous suspension of the present invention can be applied to various industrial fields including paper and pulp industries, agrochemical industries, food-processing industries, pharmaceutical industries and the like by appropriately selecting the antimicrobial compound to meet the respective requirements in the particular application from known bactericidal agents, fungicidal agents, antiseptic agents, insecticidal agents, herbicidal agents, antibiotics, pharmacologically active compounds and others.

Examples of these active compounds include isothiazolone compounds, aliphatic nitroalcohol compounds, cyanoacetamide compounds, dithiol compounds, penicillin compounds, sephem compounds, aminoglycoside compounds, macrolide compounds, lincomycin compounds, sulfonamide compounds, nitrofuran compounds, pyridone carboxylic acid compounds, tetracyclin compounds, polyene compounds, chloramphenicol compounds, phosphomycin compounds, halogenated phenol compounds, tributyl tin compounds, dialkyl dithiocarbamic acid compounds, isothiocyanate compounds and the like.

When the antimicrobial aqueous suspension of the invention is used in the field of paper industry, it is advantageous to use 2-methoxycarbonylamino benzimidazole, 2-pyridinethiol zinc-1-oxide or 2-(4-thiazolyl) benzimidazole either singly or as a combination of two kinds or more. These antimicrobial compounds are particularly effective to prevent putrefaction of the biocellulose. In the addition of these compounds to the inventive aqueous suspension with an object to prevent putrefaction of the biocellulose, the amount thereof can be as small as 50 to 2000 ppm by weight based on the amount of the biocellulose.

The use of a biocellulose as a suspending agent is not limited to the preparation of an aqueous antimicrobial suspension. For example, biocelluloses are useful as a suspending agent for foodstuff containing lactic bacteria or yeasts such as dairy products since biocelluloses serve as a nutrient for these microorganisms. In addition, biocelluloses can be used in the preparation of a water-base coating composition, e.g., paint, in the form of an aqueous suspension or emulsion.

In the following, the aqueous antimicrobial suspension of the present invention is described by way of Examples which, however, never limit the scope of the invention in any way. In the Examples, stability of the aqueous antimicrobial suspension was evaluated by visually inspecting precipitation of solid particles after lapse of 1, 10, 20 and 30 days from preparation of the suspension. The term of "parts" in the following description always refers to "parts by weight".

EXAMPLE 1

An aqueous antimicrobial suspension was prepared by vigorously and thoroughly agitating a mixture of 0.5 part of a biocellulose obtained on the market, 20.0 parts of a powder of 2-methoxycarbonylamino benzimidazole having an average particle diameter of 40 $\mu$m and 79.5 parts of deionized water. This suspension was stable without precipitation of solid particles even after 30 days of storage.

EXAMPLE 2

A second aqueous antimicrobial suspension was prepared by vigorously and thoroughly agitating a mixture of 0.5 part of the same biocellulose as used in Example 1, 10 parts of a powder of 2-methoxycarbonylamino benzimidazole having an average particle diameter of 40 $\mu$m, 10 parts of a powder of 2-pyridinethiol zinc-1-oxide having an average particle diameter of 10 $\mu$m and 79.5 parts of deionized water. This suspension was stable without precipitation of solid particles even after 30 days of storage.

COMPARATIVE EXAMPLE 1

A comparative aqueous antimicrobial suspension was prepared in the same formulation as in Example 1 excepting for the omission of the biocellulose and increase of the amount of deionized water from 79.5 parts to 80.0 parts. The suspension as prepared was a seemingly uniform dispersion of the particles while precipitation of solid particles was found on the bottom of the vessel after 24 hours of storage and settling of the solid particles was complete after 10 days of storage to form a clear supernatant on the precipitates of particles.

COMPARATIVE EXAMPLE 2

A second comparative aqueous antimicrobial suspension was prepared in the same formulation as in Example 2 excepting for the omission of the biocellulose and increase of the amount of deionized water from 79.5 parts to 80.0 parts. The suspension as prepared was a seemingly uniform dispersion of the particles while precipitation of solid particles was found on the bottom of the vessel after 24 hours of storage and settling of the solid particles was complete after 10 days of storage to form a clear supernatant on the precipitates of particles.

As is evident from the above described results, the use of a biocellulose as a suspending agent was very effective in stabilizing an aqueous suspension of solid particles without settling of the particles for more than 30 days even with a very small amount of 0.5% by weight thereof based on the overall amount of the suspension while, when the biocellulose was omitted, precipitation of the solid particles took place already after 24 hours of storage and settling of the solid particles was complete after 10 days of storage.

EXAMPLE 3

A 1 liter portion of an aqueous dispersion of a biocellulose in a concentration of 0.5% by weight was admixed under vigorous agitation with 50 ml of an aqueous dispersion of a putrefied biocellulose of the same concentration containing 200 colonies of filamentous fungi and less than 100 colonies of bacteria into a uniform blend. The aqueous dispersion was admixed with the aqueous antimicrobial suspension prepared in Example 1 or Example 2 in an amount of 200 ppm or 400 ppm by weight under agitation and the aqueous dispersions were stored under full darkness at 28° C. for 44 days to count the number of colonies of the respective microorganisms. No noticeable changes were found in the appearance of each of the suspensions.

The results of counting of the numbers of colonies are summarized in the Table below.

As a control test, the same storage test as above for 44 days was concurrently undertaken without addition of the antimicrobial suspension to find that the numbers of colonies were $3.3\times10^5$ and $6.2\times10^7$ for the filamentous fungi and for the bacteria, respectively, with remarkable discoloration in the appearance of the aqueous suspension of biocellulose.

TABLE

| Anti-microbial suspension | Concentration of suspension, ppm | Numbers of colonies | |
|---|---|---|---|
| | | Filamentous fungi | Bacteria |
| Example 1 | 200 | $2.3 \times 10^3$ | $8.9 \times 10^4$ |
| | 400 | $2.3 \times 10^3$ | $5.0 \times 10^4$ |
| Example 2 | 200 | less than 100 | less than 100 |
| | 400 | less than 100 | less than 100 |

What is claimed is:

1. An antimicrobial aqueous suspension as a uniform dispersion which comprises:

(A) an aqueous medium containing a biocellulose as the dispersion medium of the suspension; and (B) particles of an antimicrobially active, hardly water-soluble compound dispersed in the aqueous medium.

2. The antimicrobial aqueous suspension as claimed in claim 1 in which the antimicrobially active, hardly water-soluble compound is selected from the group consisting of 2-methoxy-carbonylamino benzimidazole, 2-pyridinethiol zinc-1-oxide and 2-(4-thiazolyl) benzimidazole.

3. The antimicrobial aqueous suspension as claimed in claim 1 in which the amount of the biocellulose is in the range from 0.1% to 5.0% by weight based on the overall amount of the aqueous suspension.

4. The antimicrobial aqueous suspension as claimed in claim 1 in which the component (B) is a combination of particles of 2-methoxycarbonylamino benzimidazol and particles of 2-pyridinethiol zinc-1-oxide in a weight proportion in the range from 100:1 to 1:100.

5. The antimicrobial aqueous suspension as claimed in claim 1 in which the weight proportion of the biocellulose to the component (B) is in the range from 1:300 to 10:1.

* * * * *